United States Patent [19]
Waknine

[11] Patent Number: 4,547,531
[45] Date of Patent: * Oct. 15, 1985

[54] TWO COMPONENT (PASTE-PASTE) SELF-CURING DENTAL RESTORATIVE MATERIAL

[75] Inventor: Samuel Waknine, Wallingford, Conn.

[73] Assignee: Pentron Corporation, Wallingford, Conn.

[*] Notice: The portion of the term of this patent subsequent to Oct. 1, 2002 has been disclaimed.

[21] Appl. No.: 636,970

[22] Filed: Aug. 2, 1984

[51] Int. Cl.$^4$ .......................... C08K 3/22; C08K 3/34; C08K 3/36
[52] U.S. Cl. .................................. 523/116; 433/199.1
[58] Field of Search ........................ 523/116; 433/199

[56] References Cited
U.S. PATENT DOCUMENTS
4,177,563 12/1979 Schmitz-Josten et al. .......... 523/116

Primary Examiner—John Kight
Assistant Examiner—Marvin L. Moore
Attorney, Agent, or Firm—Barry Kramer

[57] ABSTRACT

A chemically curable dental restorative material is provided comprising a two-component paste-paste system wherein:

(i) a first initiator-containing paste system comprises from about 15 to 40% by weight of a polymerizable methacrylic ester monomeric system comprising a cross-linking methacrylate monomer, at least one co-monomeric methacrylate diluent and a free radical-generating catalyst, and from about 60 to 85% by weight of an inorganic filler prepared by wet milling, surface etching milling and a silanizing milling; and (ii) a second accelerator-containing paste system comprises from about 15 to 31% by weight of a polymerizable methacrylic ester monomeric system comprising a cross-linking methacrylate monomer, at least one co-monomeric methacrylate diluent and an inorganic amine accelerator and from 69 to 85% by weight of an inorganic filler prepared by wet milling, surface etching milling and a silanizing milling;

said first and second paste systems being admixed in substantially equal proportions to form the chemically curable dental restorative material.

26 Claims, No Drawings

TWO COMPONENT (PASTE-PASTE) SELF-CURING DENTAL RESTORATIVE MATERIAL

This invention relates to an improved dental restorative composition. More particularly, this invention relates to an improved dental composite material comprising a two component (paste-paste) self curing dental restorative material, each component of which contains particles of a solid inorganic filler dispersed therein.

Historically, the dental profession has used several different types of materials for restorative dental purposes. Unfilled acrylic resins were initially used for such purposes. Acrylics, however, exhibited high coefficients of thermal expansion, e.g., $80-100 \times 10^{-6}$ mm/mm/°C.; whereas, the coefficient of thermal expansion for vital tooth structure is about $11 \times 10^{-6}$ mm/mm/°C. This disparity, coupled with high shrinkage upon polymerization, resulted in poor marginal adaptability ultimately leading to secondary decay. Moreover, the wear and abrasion characteristics as well as the overall physical and optical properties were quite poor. Silicate cements were also used for restorative purposes. The silicate cements, however, exhibited poor long term stability, a tendency to discolor and were quite brittle thereby limiting the utilization of such materials.

Subsequently, direct filling resins were developed; however, these materials suffered from excessive shrinkage upon polymerization and poor thermal expansion characteristics.

Dental composite materials comprising an inorganic filler component such as glass and an organic matrix component such as a polymerizable monomer have been available since as early as 1965. Such materials are particularly valuable when used to restore the appearance and function of teeth which have decayed, fractured, or otherwise become defective or unsightly. Composite restorative materials were developed largely through the efforts of R. L. Bowen (see, for example, U.S. Pat. No. 3,066,112; R. L. Bowen et al, "Composite Restorative Materials", paper given at 50th Anniversary Symposium on Dental Material Research, NBS, Oct. 6–8, 1969). Dental composites generally comprise an acrylic or methacrylic based system in which a silica or silicate glass filler is covalently bonded to the resin matrix, or to a coupling agent which is covalently bonded to both. With fillers used to the 70–80 weight percent level, polymerization shrinkage and thermal expansion are greatly reduced in comparison with the unfilled direct filling resins which had been previously employed. Despite the advantages of such ceramic reinforced polymeric matrix composites as compared to earlier silicate cements and direct filling resins, such composites have not been entirely satisfactory from the standpoint of resistance to abrasion and wear, ease of finishing and ease of implacement.

The fillers initially employed in dental composite materials were of a particle size ranging from about 5 to about 150 microns and were used in large amounts up to about 80% by weight of the total composition. It was found that use of such large particle size fillers resulted in rather poor mechanical properties especially, low diametral tensile strength. In addition, such compositions were very difficult to polish resulting in a relatively rough finish and frequently exhibited insufficient translucency to permit good blending of the restored tooth with adjacent teeth.

In order to overcome the deficiencies inherent in the use of such large particle size fillers, various manufacturers have recently placed on the market "microfilled" composites in which part of the filler (in the form of colloidal silica having an average particle size of about 40 millimicrons prepolymerized in an organic polymeric matrix) was admixed with a glass filler having a particle size ranging from about 5–10 microns. However, when using these relatively small particle sized fillers, only about 25 to 50% of the composite can be filler. This resulted in the overall composite exhibiting much greater shrinkage upon polymerization than the prior composites using large particle size filler, so that such composites tend to pull away from the teeth upon curing. Such "microfilled" composites, while exhibiting high polishability, were also of substantially lower diametral tensile strength than the earlier composites. Moreover, such composites have also exhibited higher coefficients of thermal expansion and higher water absorption than those of the prior composites containing larger sized particles.

The composite materials currently in commercial usage involve the conversion of monomers and/or oligomers into a polymeric matrix by chemical or photochemical initiation to form free radicals and thereby effect polymerization.

Chemical initiation is generally effected by admixing substantially equal amounts of two paste systems, one containing an initiator—usually a peroxide or other free radical-generating material and the other containing an organic amine accelerator which react to produce free radicals at the temperature in the oral cavity and thereby initiate the polymerization reaction.

Either ultraviolet or visible light can also be employed to initiate the polymerization of certain composite resin systems. Photochemical initiation provides the ultimate flexibility in placement and working with the restoration since the monomers and/or oligomers are substantially unreactive until exposed to an appropriate light source which initiates polymerization. A number of factors stemming from the use of UV light are of some concern and therefore provide an impetus for the development of improved chemically initiated composite materials. The concerns in dentistry related to ultraviolet radiation are the possibility of acute tissue injury to the patient or dental personnel and the long-term effect on viruses and cells in the mouth. Moreover, while dose and threshold level dependent, some evidence also exists for the development of photokeratitis or skin erythema due to ultraviolet radiation exposure. While there are fewer concerns about health hazards when using a visible light initiated system, there are still problems associated with photoinitiation, in general, which justify continued use of chemically cured systems. Thus, many dentists do not have a suitable light source available nor relish the expense associated with the acquisition thereof. Moreover, a light source is not always able to conveniently reach all areas of the oral cavity. Perhaps most importantly, microhardness generally decreases quite rapidly below the surface of the light cured composite resulting in a non-uniform cure as one proceeds from top to bottom of the cured composite.

Accordingly, it is an object of the present invention to provide an improved two component (paste-paste) chemically cured composite dental material which overcomes the deficiencies and disadvantages previously associated with photochemically cured composites.

It is another object of the present invention to provide an improved chemically cured composite dental material exhibiting high diametral tensile strength, X-ray opacity, excellent optical properties, excellent polishability, low water absorption and full compliance with the requirements of the American Dental Association Specification No. 27.

These as well as other objects and advantages are provided by the improved chemically curable dental restorative material of the present invention which comprises a two component paste-paste system wherein:

(i) a first initiator-containing paste system comprises from about 15 to 40% by weight of a polymerizable methacrylic ester monomeric system comprising a cross-linking methacrylate monomer, at least one co-monomeric methacrylate diluent and a free radical-generating catalyst and from about 60 to 85% by weight of an inorganic filler prepared by wet milling, surface etching milling, and a silanizing milling; and (ii) a second accelerator-containing paste system comprises from about 15 to 31% by weight of a polymerizable methacrylic ester monomeric system comprising a cross-linking methacrylate monomer, at least one co-monomeric methacrylate diluent and an organic amine accelerator and from about 69 to 85% by weight of an inorganic filler prepared by wet milling, surface etching milling, and a silanizing milling;

said first and second paste systems being admixed in substantially equal proportions to form the chemically curable dental restorative material.

It has been found in accordance with the present invention that by subjecting the inorganic filler to a specific series of milling operations, a combination of high diametral tensile strength and high polishability can be achieved in the filled, chemically cured composite resin system of the present invention as compared to prior composite dental materials employing either large particle size or submicron size fillers.

The composite dental material of the present invention comprises a unique inorganic filler having an average particle size diameter of from about 0.5 to 5 microns homogeneously dispersed in an organic chemically cured polymeric matrix.

The inorganic filler primarily comprises an X-ray opaque alkali metal or alkaline earth metal silicate such as lithium silicate, barium silicate and the like. For purposes of illustration, and as the preferred silicate species, barium silicate will hereinafter be employed as being typical of the alkali metal or alkaline earth metal silicates which can be suitably employed in the present invention. The barium silicate exhibits substantially the same index of refraction as that of the organic monomeric matrix in which it is dispersed. The filler additionally contains a relatively small amount of borosilicate glass which imparts greater compressive strength to the resulting composite and enhances the translucency thereof thereby enabling better blending of the restorative material with the adjacent teeth. In addition, the presence of the borosilicate glass helps narrow the gap between the refractive indices of the barium silicate and the organic monomeric matrix.

The ability to provide a composite dental material exhibiting both high diametral tensile strength and high polishability is achieved in accordance with the present invention by the method by which the inorganic filler is prepared. This method involves a sequence of milling operations which includes wet milling to reduce the barium silicate and borosilicate to the requisite particle size and assure a very narrow particle size distribution and to uniformly disperse the borosilicate glass particles throughout the bulk of the barium silicate. Next, in order to impart high strength characteristics to the dental composite of the present invention, the filler obtained by wet milling must undergo another milling step during which surface etching of the filler is effected. Thereafter, the wet milled and etched filler is subjected to a final milling operation during which it is generally admixed with hydrophobic colloidal fumed silica and silanized in order to render it compatible with the resin in which it will ultimately be dispersed.

The following detailed discussion will set forth methods by which the inorganic filler can be prepared, the two component (paste-paste) chemically cured methacrylic ester monomer systems can be prepared, the preparation of the ultimate composite dental material and the procedure by which the composite material is used to effect dental restoration.

Inorganic Filler Preparation (i) Wet Milling

The inorganic filler of the present invention ultimately comprises a mixture of from about 5-99% by weight of borosilicate glass, from about 1-20% by weight of colloidal fumed silica, and from about 0-75% by weight of an alkali metal or alkaline earth metal silicate, said filler having an average particle size diameter of from about 0.5 to 5 microns.

Any conventional wet milling operation can be employed to reduce the required mixture to within the desired particle size diameter range. It is considered important to prepare the mixture by a series of wet milling operations since dry milling will result in fracture of the particles with a resultant undesirable coarseness and angularity imparted to the final milled filler particles which will adversely affect the polishability of the resulting composite system.

Thus, in one embodiment, the requisite quantities of barium silicate and/or borosilicate glass, each having an average particle size of from about 7-20 microns are loaded into a suitable grinding vessel. The vessel is filled to from $\frac{1}{2}$-$\frac{3}{4}$ its volume with a suitable grinding medium. The grinding medium can comprise any low alumina, low contaminant-generating substance such as porcelain balls, stainless steel balls, borosilicate glass rods and the like. The remaining volume of the container is filled with an aqueous medium having a pH of about 5-7. The container is sealed and the contents milled and/or ground for about 8-48 hours. If borosilicate glass rods are employed as the grinding medium, sufficient borosilicate glass is abraded off the rods during the grinding operation to obviate the need to initially add borosilicate glass at the commencement of the wet milling operation. Care should be taken to avoid the introduction of any contaminants to the system either by way of the grinding medium or the aqueous medium since contaminants can give rise to cross reactions with the polymerization system imparting discoloration to the final product.

Upon completion of the wet milling operation, the barium silicate is ground to an average particle size diameter ranging between about 5-8 microns. The borosilicate glass in the mixture ranges in particle size from about 3 to 5 microns.

Illustrative of the wet milling procedures which can be employed in the present invention, borosilicate glass rods are loaded into a 5 gallon glass carboy, until the carboy is half filled. The carboy is then filled with water, sealed and tumbled at 50–350 rpm for about 16–98 hours.

The resulting conditioned borosilicate glass rods are recovered and loaded into a grinding vessel, which is mounted for continuous combined oscillatory and vibratory motion, until the vessel is ¾ filled. Typically, about 2 to 5 kilograms of X-ray opaque barium silicate glass frit having an average particle size of from about 7–20 microns, preferably about 10 microns, is charged to the vessel and then, water is added to fill the vessel. The vessel is sealed and vibrated for about 8–48 hours whereupon the barium silicate frit is ground to an average particle size ranging between about 5–8 microns and sufficient borosilicate glass is abraded off the rods to provide the requisite barium silicate/borosilicate mixture.

Thereafter, the aqueous slurry of filler is recovered and progressively strained through 200, 400 and 600 mesh screens to remove any impurities or contaminants. The resulting filtrate is subjected to vacuum filtration. The resulting cake comprising an admixture of barium silicate frit and particles of borosilicate glass which have abraded off of the borosilicate glass rods during the wet milling process is dried in a convection oven at 120° C. for about 12–36 hours. The dried, milled filler is recovered and crushed with mortar and pestle to a fine powder.

Analysis establishes that the mixture resulting from wet milling employing the techniques described hereinabove comprises from about 5–99% by weight of borosilicate glass particles having an average particle size ranging from about 3 to 5 microns and from about 0–75% by weight of barium silicate glass particles having an average particle size ranging from about 5–8 microns.

(ii) Milling with an Aqueous Etchant Solution

It has been found critical in obtaining the high strength characteristics of the composite resin of the present invention that the filler obtained by wet milling undergo another milling step during which surface etching of the filler is effected.

Most conveniently, milling in an aqueous etchant generally can be effected as follows:

a glass or glass-lined carboy is filled to one-half its volume with borosilicate glass rods which have been conditioned as set forth hereinabove. Alternatively, low alumina, porcelain balls, stainless steel balls or another low alumina, non-contaminating grinding medium can be similarly employed.

From about 2 to 4 kilograms of the dried milled filler produced by wet milling as described hereinabove is charged to the carboy along with from about 4 to 8 liters of a clear, colorless, aqueous solution of a material which will effect etching of glass, for example, bases such as NaOH, KOH, Ca(OH)$_2$, and the like; acids such as HCl, HF, and the like; and salts such as NaCl, KCl, and the like can be suitably employed. When acids are used, HF is the most preferred acid; however, certain precautions should be employed—the acid should be used in relatively dilute form, e.g., aqueous solutions containing from about 2–5% by weight of HF, and the carboy employed for further milling of the wet milled filler should be lined with an HF-resistant polymeric lining such as polyethylene or preferably, polypropylene. When bases are employed, it is considered preferable to buffer the solution to maintain a stable pH. Useful buffering agents include acetate, borate, phosphate, orothophosphate salts, and the like.

Preferably, a solution of sodium hydroxide (NaOH) buffered with mono-hydrogen sodium orthophosphate (Na$_2$HPO$_4$) and exhibiting a pH ranging from about 10–13 is employed in the etching-milling operation. A surprising increase in diametral tensile strength is imparted to the final cured composite resin by subjecting the wet milled resin to the instant etching-milling step, especially when a base is employed under the most preferred pH conditions.

The loaded carboy is sealed and tumbled at 50–350 rpm for 2–8 hours. Thereafter, the resulting milled filler is separated from the milling medium and vacuum filtered. The filter cake is continuously washed with water until pH indicators in the filtrate indicate that neutrality (5.5–7.0) has been essentially attained. The recovered filter cake is then dried in a convection oven at 120° C. for 24 hours.

It is considered important that the filter cake be essentially neutralized since any acidity or alkalinity in the final filler will impart discoloration to the ultimate resin composite.

The neutralized filter cake is then crushed to a fine powder with a mortar and pestle.

(iii) Silanizing Milling

In order for the inorganic filler to be compatible with the organic polymeric matrix, it is necessary to silanate the inorganic filler. Silanization can be effected in accordance with the present invention by once again filling a glass or glass-lined carboy to one-half its volume with conditioned borosilicate glass rods, low alumina porcelain balls, stainless steel balls or other low alumina, non-contaminating grinding medium, adding thereto from about 5 to 7 kilograms and preferably, about 6 kilograms of a solution containing from about 5 to 10 weight percent, preferably about 8% by weight, silane (SiH$_4$) in methanol; and tumbling the resulting mixture for about 2–5 minutes to uniformly disperse the grinding medium throughout the silane/methanol solution. Thereafter, from about 1 to 20% by weight, based on the weight of inorganic filler to be subsequently admixed therewith, of hydrophobic colloidal fumed silica having an average particle size diameter ranging from about 0.01 to 0.05 microns and preferably an average particle size diameter of about 0.04 microns, is added to the carboy and uniformly dispersed throughout the mixture contained therein by continuously tumbling the carboy at about 175 rpm for about an hour.

The colloidal fumed silica is of sub-micron particle size, generally exhibiting an average particle size of from about 0.01 to 0.05 micron. The use of colloidal fumed silica is important in that it introduces hydrophobicity to the resulting composite and thereby minimizes water sorption in the final composite to less than 0.7 mg/cm$^2$ as required of a type II resin by the American Dental Association Specification No. 27. In addition, the fumed silica contributes to better marginal integrity or adaptability and less marginal leakage. Also, handling characteristics such as bulk and consistency are improved. Flow and/or slump are minimized for better restoration placement in cavity preparations.

Thereafter, from about 2 to 5 kilograms, preferably about 3 kilograms, of the milled filler recovered from the wet milling and surface etching milling steps is added to the carboy and the carboy is sealed and tumbled for about 4–8 hours at 50–350 rpm to effect silanization. The slurry of silanized filler is then recovered from the carboy and subjected to vacuum filtration. The resulting filter cake is dried in a vacuum oven for one hour at 120° C. or alternatively, for 4 hours at 60° C. and then crushed by mortar and pestle giving rise to silanized filler particles having an average particle size diameter ranging from about 1 to 5 microns and preferably ranging from about 1.00 to 2.5 microns. Silanization results in from about 2–6 weight % silane preferably 2–4% silane, being coupled to the filler particles, based on total filler weight.

It is important to maintain close control over the filler average particle size. If the average particle size is lower than about 1 micron, the filler becomes too opaque and loses the translucency required to make it aesthetically compatible with the ultimate organic resin matrix. If the average particle size is higher than about 5 microns, the filler particles can separate from the ultimate organic resin matrix resulting in decreased strength of the overall composite.

Thus, the inorganic filler of the present invention comprises a mixture of from about 5–99% borosilicate, from about 1–20% colloidal fumed silica, and from about 0–75% barium silicate, said filler having an average particle size diameter of from 0.5 to about 5 microns and containing from about 2–6% silane coupled thereto, said inorganic filler having been prepared by wet milling, surface etching milling, and a silanizing milling.

The inorganic filler of the present invention as described hereinabove is preferably employed in both the initiator-containing and the accelerator-containing paste systems for composite resin systems primarily used for posterior applications, although such inorganic filler can also be employed for anterior applications as well.

It has been found, however, that for anterior applications, use of an inorganic filler comprising barium silicate, borosilicate and colloidal fumed silica as hereinabove described can result in paste systems which are too opaque for aesthetically important anterior applications. Accordingly, for anterior applications, it is considered preferable to omit the barium silicate from the initiator-containing paste system and instead, employ therein an organic filler comprising only borosilicate glass and colloidal fumed silica thereby obtaining more translucent and aesthetically pleasing pastes which results in a composite dental material which more clearly corresponds with the optical properties of adjacent anterior teeth.

The preferred inorganic filler for anterior applications can be prepared by loading alumina-free, borosilicate glass frit having an average particle size of 10 microns into a gallon glass carboy until the carboy is half filled. The carboy is then filled with water at a pH of about 5–7, sealed and tumbled at 50–350 rpm, preferably at about 175 rpm, for about 4–5 days.

Thereafter, the aqueous slurry of filler is recovered and progressively strained through 200, 400 and 600 mesh screens to remove any impurities or contaminants with subsequent sieving through a 10 micron nylon mesh. The resulting filtrate is subjected to vacuum filtration. The resulting cake is dried in a convection oven at 120° C. for about 12–36 hours. The dried, milled filler is recovered and crushed with mortar and pestle to a fine powder having an average particle diameter of about 0.5–5 microns.

The resulting borosilicate glass particles are subjected to surface etching milling and silanized in the same manner described hereinabove to obtain an inorganic filler to which has been coupled from about 2–6 weight % silane, preferably 2–5% silane based on total filler weight. Said filler is especially useful in composite compositions employed primarily for anterior restorations although, such inorganic fillers can be employed for posterior applications as well.

As compared with the inorganic filler used primarily for posterior applications, the inorganic filler used primarily for anterior applications, as prepared, consists essentially of silanized borosilicate glass. Colloidal fumed silica in amounts of from about 1–5% by weight is prepolymerized into the initiator paste system when the inorganic filler and polymerizable initiator-containing monomeric system are admixed together as hereinafter described instead of during the milling processes employed to prepare the inorganic filler used primarily for posterior applications.

Preparation of the Catalyst and Accelerator Paste Systems

Both the catalyst and accelerator paste systems contain several similar components, i.e., the primary polymerizable monomeric methacrylic esters, other mono-, di-, or trimethacrylate monomers as diluents, antioxidants, and coloring agents.

Any non-toxic organic monomer useful in dental composite restorative compositions can be employed in conjunction with the inorganic fillers of the present invention.

The most commonly employed monomers are generally monomeric methacrylic esters. Because of an excellent combination of physical properties, i.e., diametral tensile strength, water sorption, index of refraction, shrinkage, and lack of toxicity and/or biocompatibility, most commercially available dental composite resins are based on use of a cross-linking monomer or polymer such as methacrylates, polyurethanes and the like. Preferably, the monomeric reaction product of 4,4'-isopropylidenediphenol and glycidyl methacrylate, commonly referred to as "BIS-GMA" or derivatives thereof are employed. Other suitable cross-linking monomers or polymers include hydroxyethoxy methacrylate, the reaction product of 4-methacryoyloxyethyl trimellitc anhydride and tributyl borane, ethoxylated bisphenol-A dimethacrylate, the addition product of N-phenylglycine and glycidyl methacrylate, the addition product of N-tolylglycine and glycidyl methacrylate, the addition product of pyromellitic dianhydride and 2-hydroxyethyl methacrylate, polyurethane methacrylate and other urethane polymers, and the like.

Additionally, other monomethacrylate, dimethacrylate and trimethacrylate monomers can be used as diluents to reduce the viscosity of the polymerization medium. Typically, a dimethacrylate comonomer such as triethylene glycol dimethacrylate, commonly referred to as "TEGDM" is preferably employed since it provides a higher marginal adaptability index. Other suitable co-monomeric methacrylates include ethylene glycol dimethacrylate, tetramethylene glycol dimethacrylate, trimethylolpropyl trimethacrylate, 1,6-hexanediol dimethacrylate, 1,3-butanediol dimethacrylate, and the like.

In order to obtain an essentially color free dental restorative material, it is considered preferable to employ monomers and diluents which are substantially color-free exhibiting an APHA color range less than about 50 thereby appearing as clear and colorless as water.

Each polymerization system also includes an antioxidant to prevent premature polymerization thereby increasing the shelf life of the two paste systems. Typically, 4-methoxyphenol, 2,6-di-tert-butyl 4-methyl phenol (BHT), and other hindered phenols can be suitably employed. The antioxidants are incorporated in each paste system in an amount ranging from about 0.05 to about 0.50 percent by weight of the polymerization systems. It is generally considered preferable to employ more antioxidant in the initiator paste system because of the presence of the free radical-generating initiator. Generally, the amount of antioxidant in the initiator paste system ranges from about 0.1 to 0.2 percent by weight of the polymerization system.

The initiator resin system comprises from about 20 to 80% by weight of a polymerizable monomeric methacrylic ester, from about 5 to 60% by weight of at least one co-monomeric methacrylate diluent, from about 0.05 to 0.50% by weight of an antioxidant and from about 1 to 7% by weight of a free radical-generating initiator. The free radical-generating initiator is a material which is capable of generating free radicals at room temperature in the presence of a suitable accelerator. Generally, such initiators as benzoyl peroxide, lauroyl peroxide, tert.-butyl hydroperoxide and the like can be suitably employed. Preferably, the initiator employed is of high purity, e.g., 99.9% pure. for example, LUCIDOL, a benzoyl peroxide initiator available from Pennwalt Corporation, Philadelphia, Pa., has been found suitable because of its high purity.

The accelerator resin system comprises from about 20 to 80% by weight of a polymerizable monomeric methacrylic ester, from about 5 to 60% by weight of at least one co-monomeric methacrylate diluent, from about 0.05 to 0.50% by weight of an antioxidant and from about 0.5 to 4% by weight of a tertiary aromatic amine accelerator. Tertiary aromatic amines such as N,N-dimethyl-p-toluidene, N,N-dihydroxyethyl-p-toluidine, and the like react with the initiator at room temperature to generate free radicals and thereby initiate the polymerization reaction. The accelerator must be extremely pure otherwise it will introduce undesirable color to the ultimate composite. Thus, for example, when N,N-dihydroxyethyl-p-toluidine is employed, it is considered preferable to first dissolve the material in a suitable solvent, recrystallize it and isolate the recrystallized product which exhibits a melting point of 53.5°-54.5° C.

In addition, the accelerator resin system also contains from about 1 to 8% by weight of an ultraviolet absorber. Typically, ultraviolet absorbers are benzophenones, benzotriazoles and derivatives thereof such as UV-9, a benzotriazole ultraviolet absorber available from American Cyanamid Company, Wayne, N.J., TINUVIN P, a benzotriazole ultraviolet absorber available from Ciba-Geigy Corporation, Ardsley, N.Y. and the like. Ultraviolet absorbers absorb incident ultraviolet light and thereby improve the color stability of the ultimate restoration.

It is considered preferable that each component of the polymerization system be selected from as high purity stocks as are commercially available since contaminants can give rise to cross reactions between the initiator and accelerator discoloring the final resin product.

The above unfilled monomeric systems can be used per se, and, when admixed together in substantially a 1:1 ratio, form a bonding agent for the filled composite resin system of the present invention in the actual restoration process as set forth hereinafter.

If desired, the unfilled monomeric systems of the present invention can be tinted to any of the desired universal colors by incorporating in each of the unfilled monomeric systems trace amounts of any FDA and FDC approved, low alumina dye, pigment, and lakolene (low dye) preparations such as carbon black, yellow No. 5, yellow No. 6, and the like as well as mixtures thereof. The dye, pigment or lakolene preparations can be easily homogeneously dispersed within the unfilled monomeric systems by ultrasonification or other mixing techniques thereby providing better color stability.

Preparation of the Filled Composite Restorative Material

The filled composite restorative materials of the present invention can be prepared in situ by homogeneously admixing substantially equal parts of the filled initiator paste system and the filled accelerator paste system.

The filled initiator paste system and the filled accelerator paste system can each be prepared by admixing from about 15 to 40% by weight, preferably, 18 to 33% by weight, and most preferably 18 to 22% by weight, of the unfilled polymerizable monomeric initiator and accelerator systems described hereinbefore with from about 60 to 85% by weight, preferably 67 to 82% by weight, and most preferably 78 to 82% by weight, of the treated inorganic filler prepared in the manner hereinabove described.

For primarily posterior applications, the inorganic filler, as prepared, contains from about 5-20% by weight of borosilicate glass, from about 10-20% by weight of colloidal fumed silica, and from about 60-85% by weight of barium silicate.

For primarily anterior applications, the inorganic filler, as prepared, comprises only the borosilicate glass to which has been coupled from about 2-6% by weight silane. It is considered preferable, however, to add from about 1-5% by weight of colloidal fumed silica to the initiator paste system during preparation thereof. The colloidal fumed silica is of sub-micron particle size, generally exhibiting an average particle size of from about 0.01 to 0.05 micron. The use of colloidal fumed silica is important in that it contributes to the hydrophobicity of the resulting composite and thereby minimizes water sorption in the final composite to less than 0.7 mg/cm$^2$ as required of a type II resin by the American Dental Association Specification No. 27. In addition, the colloidal fumed silica contributes to better marginal integrity or adaptability and less marginal leakage. Also, handling characteristics such as bulk and consistency are improved. Flow and/or slump are minimized for better restoration placement in cavity preparations. The fumed silica is preferably admixed with the unfilled initiator polymerization system until a homogeneous mixture is obtained.

The treated inorganic filler, whether for anterior or posterior applications is admixed with the appropriate initiator and/or accelerator monomeric systems in a planetary mixer under vacuum to form homogeneous pastes. The resulting pastes can be passed through a two roll stainless steel mill, if desired, to ensure homogeneity. The resulting pastes can then be packaged in appropriate packaging which permits easy dispensing-such as in syringes. The dental restorative material of the present invention thus comprises a two component system—a filled initiator paste system and a filled accelerator paste system which, when combined in substantially equal amounts, provide a self-curing, highly efficacious dental composite.

Restorative Dental Procedure

The filled composite resins of the present invention, as formulated for anterior use, can be used in Class III and V restorations and for limited use in Class I restorations in premolars and selected Class IV restorations where aesthetics are of primary importance. The filled composite resins, as formulated for posterior use, can be used in Class I and II restorations.

Conventional cavity preparation techniques can be employed. Cavosurface margin can be either beveled or butt joint form—the latter repairing a slight overfill and then contoured to a featheredge.

Acid etching of the enamel can be effected by applying an aqueous orthophosphoric acid solution or preferably, a gel containing about 35-40%, preferably 37% by weight, orthophosphoric acid to the enamel surface with a small cotton pellet. Care should be taken to avoid cavity preparations. Generally, use of a continuous slow and gentle application for 60 seconds on permanent teeth and 90 seconds on deciduous teeth is sufficient. Pressure should be avoided which would destroy the retentive characteristics of the etched surface. A visible layer of the acid solution should be present at all times during the etching. Additional solution may be required to maintain a visible layer. The acid solution should never be allowed to dry out on the tooth surface. After etching, the area should be well washed with water. A rubber dam can be appropriately placed in position to make sure that no acid is ingested by the patient during washing or gingival tissue irritated. Thereafter, the area should be dried thoroughly with warm, oil-free air. A properly etched tooth will have a dull, whitish appearance. For bonding and sealing Class I, III and V restorations, the enamel should, if possible be conditioned at least one millimeter beyond the margin of the cavity preparation. For Class IV restorations, the etched area should be at least as wide as the tooth structure being replaced, but never less than two millimeters.

The dry cavity preparation should be lined with any conventional calcium hydroxide preparation. Use of zinc oxide/eugenol should be avoided. After the calcium hydroxide hardens, an extremely thin layer of bonding agent i.e., the system resulting from admixing substantially equal amounts of the unfilled initiator system and the unfilled accelerator system, should be applied over the etched enamel and the previously applied layer of calcium hyroxide. An extremely thin layer is obtained by removing the excess bonding agent from the enamel surface by a brush or similar means. The bonding agent is then allowed sufficient time to polymerize which generally takes from about 2 to 5 minutes before further working on the teeth can be effected.

Thereafter, the filled composite resin of the present invention is prepared in situ by admixing substantially equal amounts of the initiator and accelerator paste systems. The resulting composite is placed into the cavity preparation while also assuring a proper featheredge extension thereof onto the etched enamel beyond the cavity margin or fracture line. In addition to manual shaping and contouring, strips and crown forms may be used to restore anatomic form and minimize the amount of excess to be removed. Matrix strips are recommended to contain and shape the restorative compositions in appropriate cavity preparations, i.e. Class III, IV and V restorations.

It has been found that generally a homogeneous admixture of the initiator paste system and the accelerator paste system can be achieved by thoroughly admixing the two paste systems for from about 30 seconds to about 1.0 minute. The resulting composite should be immediately placed into the cavity preparation and shaped into the desired anatomic form in from about 1.0 to 2.0 minutes after the admixture was initially prepared. The composite will set within about 2 to 5 minutes after the admixture was initially prepared enabling any desired trimming and/or polishing operations to be effected immediately thereafter. Complete curing and full strength are achieved within 24 hours. If desired, or necessary, after the composite has set, the restored area can be trimmed with carbide aesthetic trimmers and subsequently with low grit diamonds and pre-polished and ultimately polished with green rubber wheels, caps, cones or Sof-Lex discs.

The filled chemically cured composite restorative system of the present invention is especially useful for caries, fractures, lesions, chipping, lengthening, restoring or reconstructing, modification of tetracycline stained teeth, cervical erosion, veneers and the like.

The following examples further illustrate the present invention. Unless otherwise stated, all percentages and parts are by weight.

EXAMPLE 1

A chemically cured dental restorative material suitable for posterior applications was prepared as follows:

Borosilicate glass rods, available from Corning Glass Works, Corning, N.Y., are cut into cylindrical form. The resulting cylinders are loaded into a 5 gallon glass carboy until the carboy is ½ filled. The carboy is then filled with water, sealed and tumbled at 175 rpm for 48 hours to condition the glass rods.

The conditioned borosilicate glass rods are recovered and loaded into a 5 gallon polyvinylidene fluoride lined grinding vessel adapted for combined oscillatory and vibratory motion. The grinding vessel is loaded with the glass rods until ¾ filled. Three kilograms of X-ray opaque barium silicate glass frit (Essington, Pa.) having an average particle size diameter of 10 microns are added to the grinding vessel and then water is added to fill the grinding vessel. The vessel is then sealed and vibrated for 24 hours whereupon the barium silicate frit is ground to an average particle size diameter ranging between about 5-6 microns and sufficient borosilicate glass is abraded off the rods to provide a barium silicate-borosilicate glass mixture comprising 89% barium silicate and 11% borosilicate glass.

The resulting aqueous slurry is recovered and strained through a series of 200, 400 and 600 mesh screens and a 10 micron nylon mesh screen. The resulting filtrate is subjected to vacuum filtration and then dried in a convection oven at 120° C. for 24 hours. The dried, milled filler is recovered and crushed and ground with a mortar and pestle to a fine powder.

Three kilograms of the dried, milled filler are charged to a glass carboy which is filled to one-half its volume with conditioned borosilicate glass rods prepared as described above. The carboy is then filled with six liters of a clear, colorless, aqueous solution of sodium hydroxide exhibiting a pH of 12 which is buffered with $Na_2HPO_4$. The loaded carboy is sealed and tumbled at 175 rpm for 4 hours. Thereafter, the resulting milled filler is recovered and subjected to vacuum filtration. The filter cake is washed with water until pH indicators in the filtrate indicate neutrality (pH=5.5-7.0) has been essentially obtained. The recovered filter cake is then dried in a convection oven at 120° C. for 24 hours. The neutralized filter cake is ground to a fine powder with a mortar and pestle. Milling with an aqueous etchant under controlled pH conditions in the manner set forth above imparts increased surface porosity to the filler particles.

Silanization of the filler thus obtained is effected by filling a 5 gallon glass carboy to one-half its volume with borosilicate glass rods conditioned in the manner described hereinabove. Six kilograms of a solution of 8% silane in methanol is charged to the carboy and tumbled for about 5 minutes to uniformly disperse the conditioned borosilicate rods throughout the silane/methanol solution. Thereafter, 450 grams of hydrophobic colloidal fumed silica having an average particle size of about 0.04 microns is charged to the carboy and uniformly dispersed throughout the mixture contained therein by continuously tumbling the carboy at 175 rpm for an hour. Three kilograms of the milled filler recovered from the prior milling steps is then charged to the carboy. The carboy is sealed and tumbled for an additional 6 hours at 175 rpm. The silanized slurry is recovered and subjected to vacuum filtration. The resulting filter cake is dried in a vacuum oven for one hour at 120° C. and then pulverized with mortar and pestle giving rise to silanized filler particles having an average particle size of 1.4 microns. Silanization results in 2-6% silane being coupled to the filler particles, preferably about 3.5% silane.

The initiator resin system was prepared by admixing the following:
55.00 grams Bis-GMA
45.00 grams Triethyleneglycol dimethacrylate (TEGDM)
0.15 grams BHT
4.00 grams LUCIDOL benzoyl peroxide In the above liquid monomeric composition was dispersed a trace of color to impose a desired universal color to the composition. The initiator paste system was obtained by admixing 21% by weight of the above liquid monomeric composition with 79% by weight of the treated inorganic filler obtained in the foregoing manner in a planetary mixer under vacuum forming a homogeneous paste. The paste was passed through a two roll stainless steel mill to ensure homogeneity.

The accelerator resin system was prepared by admixing the following:
55.00 grams Bis-GMA
45.00 grams Triethyleneglycol dimethacrylate
0.15 grams BHT
1.50 grams dihydroxyethyl p-toluidene (m.p.:53.5°-54.5° C.)
4.00 grams UV-9 benzotriazole In the above liquid monomeric composition was dispersed a trace of colorant to impose the same universal color to the composition as was imparted to the initiator paste system. The accelerator paste system was obtained by admixing 21% by weight of the above liquid monomeric composition with 79% by weight of the treated inorganic filler obtained as described above in a planetary mixer under vacuum forming a homogeneous paste. The paste was passed through a two roll stainless steel mill to ensure homogeneity.

Essentially equal amounts of the foregoing initiator paste system and accelerator paste system were uniformly admixed for about one minute to form the filled composite restorative material of the present invention. Samples of the composite material admixture were loaded into 6 mm. diameter×3 mm. stainless steel split cylindrical molds, set on 25×75 mm. glass microslides, condensed with a stainless steel spatula and covered with glass cover microslips 25×25 mm. The samples were cured in a 37° C.±0.1° C., 99.9±0.1% relative humidity chamber for 15 minutes. Then the units were disassembled from the molds, polished with a 240 or finer silicon carbide strip and subjected to diametral compression on an Instron machine to obtain the 15 minute diametral tensile strength (DTS). In similar fashion, samples were cured for 24 hours and then subjected to diametral compression.

The diametral tensile strength and the compressive strength measured in accordance with the American Dental Association (ADA) Specification No. 27 were as follows (values reported are the average of six specimens):

|  | 15 minutes | 24 hours |
| --- | --- | --- |
| Diametral Tensile Strength (psi) | 7,000 | 10,000 |
| Compressive Strength (psi) | 59,000 | 65,000 |

In accordance with ADA Specification No. 27, the Barcol Hardness of the cured composites was determined to be 96.0, the water sorption was found to be 0.4 mg/cm$^2$/week, thermal expansion 14.14 mm/mm/°C.×10$^{-6}$ and shrinkage of about 0.25%. In addition, the composites met the UV stability requirements of ADA specification No. 27. The composites exhibited a working time of 30-45 seconds (mixing time), a set time of 2.5-2.75 minutes and a hardening time of 5 minutes, all as measured from initial admixture of the initiator and accelerator paste systems. The extremely low water sorption and excellent mechanical properties are attributable, in part, to the relatively high ratio of Bis-GMA to TEGDM employed.

In addition to the foregoing physical properties, the composites were found to exhibit excellent radiopacity, abrasion resistance, compatability with high grade stainless steel instruments such as stainless steel cement spatulas No. 324, carvers, and the like and are not susceptible to discoloration through use of such stainless steel instruments.

Sliding wear and fatigue tests established the excellent wear resistance of these composites.

The high consistency, i.e., high viscosity, of these composites enables proper condensation into Class I and II restorations.

The mechanical, physical, thermal and rheological properties of the instant composites enhance marginal adaptability—integrity and proper sealing; therefore, minimizing contraction gaps, micro-leakage, wear, premature fracture and ultimately, secondary decay.

EXAMPLE 2

A chemically cured dental restorative material suitable for anterior applications was prepared as follows:

The accelerator paste system was prepared in the identical manner described in Example 1, except that only 1.00 gram of dihydroxyl p-toluidene was employed.

The initiator paste system was prepared as follows:

Alumina-free, borosilicate glass frit having an average particle size of 10 microns was charged to a 1M³ vibratory grinding vessel until the vessel was half filled therewith. The vessel was then filled with water at a pH of about 7, sealed and vibrated for 24 hours. Thereafter, the aqueous slurry of filler was recovered and progressively strained through 200, 400 and 600 mesh screens to remove any impurities. The filtrate was subjected to vacuum filtration and the resulting cake was dried in a convection oven at 120° C. for about 24 hours. The dried, milled filler was recovered and crushed with mortar and pestle to a fine powder having an average particle diameter of about 4–8 microns.

Three kilograms of the dried, milled filler are charged to a glass carboy which is filled to one-half its volume with conditioned borosilicate glass rods prepared as described above. The carboy is then filled with six liters of a clear, colorless, aqueous solution of sodium hydroxide exhibiting a pH of 12 which is buffered with $Na_2HPO_4$. The loaded carboy is sealed and tumbled at 175 rpm for 4 hours. Thereafter, the resulting milled filler is recovered and subjected to vacuum filtration. The filter cake is washed with water until pH indicators in the filtrate indicate neutrality (pH=5.5–7.0) has been essentially obtained. The recovered filter cake is then dried in a convention oven at 120° C. for 24 hours. The neutralized filter cake is ground to a fine powder with a mortar and pestle. Milling with an aqueous etchant under controlled pH conditions in the manner set forth above imparts increased surface porosity to the filler particles.

Silanization of the filler thus obtained was effected by filling a 5 gallon glass carboy to one-half its volume with borosilicate glass rods conditioned in the manner described hereinbefore. Six kilograms of a solution of 8% silane in methanol was charged to the carboy and tumbled for about 5 minutes to uniformly disperse the conditioned borosilicate rods throughout the silane/methanol solution. Thereafter, 3 kilograms of the milled borosilicate glass filler recovered from the above wet milling step was charged to the carboy. The carboy was sealed and tumbled for 6 hours at 175 rpm. The silanized slurry was recovered and subjected to vacuum filtration. The filter cake was dried in a vacuum oven for one hour at 120° C. and then crushed with mortar and pestle giving rise to silanized filler particles having an average particle size of 2 microns. Silanization results in 3.5% silane being coupled to the filler particles.

The initiator resin system was prepared by admixing the following:
55.00 grams Bis-GMA
45.00 grams Triethyleneglycol dimethacrylate
0.15 grams BHT
4.00 grams LUCIDOL benzoyl peroxide In the above liquid monomeric composition was dispersed a trace of colorant to impart the same universal color as employed in the accelerator paste system. The initiator paste system was obtained by admixing 29.5% by weight of the above liquid monomeric composition with 68.5% by weight of the treated borosilicate filler and 2% by weight of colloidal fumed silica in a planetary mixer under vacuum forming a homogeneous paste. The paste was passed through a two roll stainless steel mill to ensure homogeneity.

Essentially equal amounts of the foregoing initiator paste system and the accelerator paste system were uniformly admixed for about one minute to form the filled composite restorative material of the present invention.

Samples of the composite restorative material so prepared were evaluated in the same manner as in Example 1 with the following results:

|  | 15 minutes | 24 hours |
|---|---|---|
| Diametral Tensile Strength (psi) | 7,000 | 8,000 |
| Compressive Strength (psi) | 54,400 | 60,000 |
| Barcol Hardness | 96.0 | |
| Water Sorption | 0.4 mg/cm²/week | |
| Thermal Expansion | 14.32 mm./mm./°C. × $10^{-6}$ | |
| Shrinkage | 0.25% | |
| Working Time | 30–45 sec. | |
| Set Time | 2.5–2.75 min. | |
| Hardening Time | 5.00 min. | |

In addition to the foregoing physical properties, the composites were found to exhibit excellent radiopacity, abrasive resistance, compatability with high grade stainless steel instruments such as stainless steel cement spatulas No. 324, carvers and the like and are not susceptible to discoloration through use of such stainless steel instruments.

As shown from the foregoing examples, the self-curing filled composite restorative systems provided by the present invention overcome the deficiencies inherent in the use of large particle size fillers as heretofore employed. Moreover, the composites of the present invention do not exhibit the deficiencies characteristic of the use of microfilled systems; namely, low diametral tensile strength, high water sorption, high shrinkage and high thermal expansion upon curing. In fact, the composite restorative systems of the present invention exhibit thermal expansion characteristics which closely approximate the thermal expansion characteristics of vital tooth structure. In addition, the composites of the present invention provide X-ray opacity, excellent optical properties, excellent polishability and full compliance with the requirements of the American Dental Association Specification No. 27, Type II.

What is claimed is:

1. A chemically curable dental restorative material comprising a two-component paste-paste system wherein:
   (i) a first initiator-containing paste system comprises from about 15 to 40% by weight of a polymerizable methacrylic ester monomeric system comprising a cross-linking methacrylate monomer, at least one co-monomeric methacrylate diluent and a free radical-generating catalyst, and from about 60 to 85% by weight of an inorganic filler prepared by wet milling, surface etching milling, and a silanizing milling; and
   (ii) a second accelerator-containing paste system comprises from about 15 to 31% by weight of a polymerizable methacrylic ester monomeric system comprising a cross-linking methacrylate monomer, at least one co-monomeric methacrylate diluent and an inorganic amine accelerator and from 69 to 85% by weight of an inorganic filler prepared by wet milling, surface etching milling, and a silanizing milling;
   said first and second paste systems being admixed in substantially equal proportions to form the chemically curable dental restorative material.

2. The chemically curable dental restorative material as defined in claim 1 wherein the inorganic filler in each of the paste systems exhibits an average particle size diameter of from about 0.5 to 5 microns.

3. A chemically curable dental restorative material as defined in claim 2 wherein the inorganic filler in each paste system comprises a mixture of from about 5–99% by weight of borosilicate glass, from about 1–20% by weight of colloidal fumed silica, and from about 0–75% by weight of an alkali metal or alkaline earth metal silicate, said inorganic filler containing from about 2–6% silane coupled thereto.

4. A chemically curable dental restorative material as defined in claim 1 wherein the inorganic filler in the first initiator-containing paste system consists essentially of borosilicate glass to which has been coupled from about 2–6 weight percent silane and said initiator-containing paste system additionally contains from about 1–5% by weight of colloidal fumed silica.

5. A chemically curable dental restorative material as defined in claim 1 wherein the cross-linking methacrylate monomer employed in each paste system is the reaction product of 4,4′-isopropylidenediphenol and glycidyl methacrylate.

6. A chemically curable dental restorative material as defined in claim 1 wherein the co-monomeric methacrylate diluent employed in each paste system is triethyleneglycol dimethacrylate.

7. A chemically curable dental restorative material as defined in claim 1 wherein the cross-linking methacrylate monomer and co-monomeric methacrylate diluent are substantially color-free exhibiting an APHA color range less than about 50.

8. A chemically curable dental restorative material as defined in claim 1 wherein each paste system additionally contains an antioxidant.

9. A chemically curable dental restorative material as defined in claim 8 wherein the antioxidant is 2,6-di-tert-butyl 4-methylphenol.

10. A chemically curable dental restorative material as defined in Claim 1 wherein the polymerizable methacrylic ester monomeric system of the first initiator-containing paste system comprises from about 20 to 80% by weight of a polymerizable monomeric methacrylic ester, from about 5 to 60% by weight of at least one co-monomeric methacrylate diluent, from about 0.05 to 0.50% by weight of an antioxidant and from about 1 to 7% by weight of a free radical-generating initiator.

11. A chemically curable dental restorative material as defined in claim 10 wherein the amount of antioxident ranges from about 0.1 to 0.2% by weight of said polymerization system.

12. A chemically curable dental restorative material as defined in claim 10 wherein the free radical generating initiator is a peroxide initiator.

13. A chemically curable dental restorative material as defined in claim 12 wherein the peroxide initiator is benzoyl peroxide.

14. A chemically curable dental restorative material wherein the polymerizable methacrylic ester monomeric system of the second accelerator-containing paste system comprises from about 20 to about 80% by weight of a polymerizable monomeric methacrylic ester, from about 5 to 60% by weight of at least one co-monomeric methacrylate, from about 0.05 to 0.50% by weight of an antioxidant and from about 0.5 to 4% by weight of a tertiary aromatic amine accelerator.

15. A chemically curable dental restorative material as defined in claim 14 wherein the teritary aromatic amine accelerator is N,N-dihydroxyethyl-p-bis-toluidine having a melting point of 53.5°–54.5° C.

16. A chemically curable dental restorative material as defined in claim 14 wherein the second accelerator-containing paste additionally contains from about 1 to 8% by weight of an ultraviolet absorber.

17. A chemically curable dental restorative material as defined in claim 16 wherein the ultraviolet absorber is a member selected from the group consisting of benzophenones and benzotriazoles.

18. A chemically curable dental restorative material as defined in claim 1 wherein the polymerizable methacrylic ester monomeric system of each paste system additionally contains trace amounts of a low alumina dye, pigment or lakolene preparation.

19. A chemically curable dental restorative material as defined in claim 1 wherein each paste system comprises from about 18 to 33% by weight of the polymerizable methacrylic ester monomeric system and from about 67 to 82% by weight of the inorganic filler.

20. A chemically curable dental restorative material for posterior applications which comprises a two component paste-paste system wherein:
   (i) the first initiator-containing paste system comprises (a) about 18 to 22% by weight of a polymerizable methacrylic ester monomeric system comprising 52.81% by weight of the reaction product of 4,4′-isopropylidenediphenol and glycidyl methacrylate, 43.21% by weight of triethyleneglycol dimethacrylate, 0.14% by weight of 2,6-di-tert-butyl 4-methylphenol and 3.84% by weight of benzoyl peroxide and (b) about 78 to 82% by weight of an inorganic filler prepared by wet milling, surface etching milling, and a silanizing milling comprising a mixture of from about 5–20% borosilicate, from about 10–20% colloidal fumed silica, and from about 60–85% barium silicate, said inorganic filler having an average particle size diameter of from about 0.5 to about 5 microns and containing from about 2–6% silane coupled thereto; and
   (ii) the second accelerator-containing paste system comprises (a) about 18 to 22% by weight of a polymerizable methacrylic ester monomeric system comprising 52.06% by weight of the reaction product of 4,4′-isopropylidene diphenol and glycidyl methacrylate, 42.59% by weight triethyleneglycol dimethacrylate, 0.14% by weight 2,6-di-tert-butyl 4-methylphenol, 1.42% by weight dihydroxyethyl p-toluidene and 3.79% by weight of a benzotriazole, and (b) about 78 to 82% by weight of an inorganic filler prepared by wet milling, surface etching milling and a silanizing milling which comprises a mixture of from about 5–20% borosilicate, from about 10–20% colloidal fumed silica, and from about 60–85% barium silicate, said filler having an average particle size diameter of from 0.5 to about 5 microns and containing from about 2–6% silane coupled thereto;
   said first and second paste systems being admixed in substantially equal proportions to form the chemically curable dental restorative material.

21. A chemically curable dental restorative material for anterior applications comprising a two component paste-paste system wherein:
   (i) the first initiator-containing paste system comprises (a) about 27.5 to 31.5% by weight of a polymerizable methacrylic ester monomeric system comprising 52.81% by weight of the reaction product of 4,4'-isopropylidenediphenol and glycidyl methacrylate, 42.21% by weight of triethyleneglycol dimethacrylate, 0.14% by weight of 2,6-di-tert-butyl 4-methylphenol, and 3.84% by weight of benzoyl peroxide; (b) about 63.5 to 71.5% by weight of a borosilicate filler prepared by wet milling, surface etching milling and a silanizing milling and having an average particle size of about 2.0 microns and further having about 3.5% silane coupled thereto; and (c) 1 to 5% by weight of colloidal fumed silica; and (ii) the second accelerator-containing paste system comprises (a) about 18 to 22% by weight of a polymerizable methacrylic ester monomeric system comprising 52.31% by weight of the reaction product of 4,4'-isopropylidene diphenol and glycidyl methacrylate, 42.80% by weight triethyleneglycol dimethacrylate, 0.14% by weight 2,6-di-tert-butyl 4-methylphenol, 0.95% by weight dihydroxyethyl p-toluidene and 3.80% by weight of a benzotriazole, and (b) about 78 to 82% by weight of an inorganic filler prepared by wet milling, surface etching milling, and a silanizing milling which comprises a mixture of from about 5–20% borosilicate, from about 10–20% colloidal fumed silica, and from about 60–85% barium silicate, said filler having an average particle size diameter of from 0.5 to about 5 microns and containing from about 2–6% silane coupled thereto;

said first and second paste systems being admixed in substantially equal proportions to form the chemically curable dental restorative material.

22. A chemically curable dental restorative material for posterior applications exhibiting a thermal expansion ranging from about 12–14.5 mm./mm./°C.×10$^{-6}$ which comprises a two component paste-paste system wherein:

(i) the first initiator-containing paste system comprises (a) about 18 to 22% by weight of a polymerizable methacrylic ester monomeric system comprising from about 20% to 80% by weight of a polymerizable monomeric methacrylic ester, from about 5 to 60% by weight of at least one co-monomeric methacrylate diluent, from about 0.05 to 0.5% by weight of an antioxidant and from about 1 to 7% by weight of a free radical-generating initiator and (b) about 78 to 82% by weight of an inorganic filler comprising a mixture of from about 10–20% by weight of colloidal fumed silica, 5–20% by weight of borosilicate glass, and from about 60–85% by weight of an alkali metal or alkaline earth metal silicate, said inorganic filler containing from about 2–6% silane coupled thereto, said filler prepared by wet milling, surface etching milling and a silanizing milling; and (ii) the second accelerator-containing paste system comprises (a) about 18 to 22% by weight of a polymerizable methacrylic ester monomeric system comprising from about 20 to about 80% by weight of a polymerizable monomeric methacrylate ester, from about 5 to 60% by weight of at least one co-monomeric methacrylate, from about 0.05 to 0.50% by weight of an antioxidant and from about 0.5 to 4% by weight of a tertiary aromatic amine accelerator, and (b) about 78 to 82% by weight of an inorganic filler comprising a mixture of from about 10–20% by weight of colloidal fumed silica, 5–20% by weight of borosilicate glass and from about 60–85% by weight of an alkali metal or alkaline earth metal silicate, said inorganic filler containing from about 2–6% silane coupled thereto, said filler prepared by wet milling, surface etching milling and a silanizing milling;

said first and second paste systems being admixed in substantially equal proportions to form the chemically curable dental restorative system.

23. A chemically curable dental restorative material as defined in claim 22 wherein the second accelerator-containing paste additionally contains from about 1 to 8% by weight of an ultraviolet absorber.

24. A chemically curable dental restorative material for anterior applications exhibiting a thermal expansion ranging from about 12–14.5 mm./mm./°C.×10$^{-6}$ which comprises a two component paste-paste system wherein:

(i) the first initiator-containing paste system comprises (a) about 27.5 to 31.5% by weight of a polymerizable methacrylic ester monomeric system comprising from about 20% to 80% by weight of a polymerizable monomeric methacrylic ester, from about 5 to 60% by weight of at least one co-monomeric methacrylate diluent, from about 0.05 to 0.5% by weight of an antioxidant and from about 1 to 7% by weight of a free-radical generating initiator; (b) about 63.5 to 71.5% by weight of a borosilicate filler prepared by wet milling, surface etching milling and a silanizing milling and having about 2–4.5% silane coupled thereto; and (c) 1–5% by weight of colloidal fumed silica; and (ii) the second accelerator-containing paste system comprises (a) about 18 to 22% by weight of a polymerizable methacrylic ester monomeric system comprising from about 20% to 80% by weight of a polymerizable monomeric methacrylate ester, from about 5 to 60% by weight of at least one co-monomeric methacrylate, from about 0.05 to 0.50% by weight of an antioxidant and from about 0.5 to 4% by weight of a tertiary aromatic amine accelerator, and (b) about 78 to 82% of an inorganic filler comprising a mixture of from about 10–20% by weight of colloidal fumed silica, 5–20% by weight of borosilicate glass and from about 60–85% by weight of an alkali metal or alkaline earth metal silicate, said inorganic filler containing from about 2–6% silane coupled thereto, said filler prepared by wet milling, surface etching milling and a silanizing milling;

said first and second paste systems being admixed in substantially equal proportions to form the chemically curable dental restorative system.

25. A chemically curable dental restorative material as defined in claim 24 wherein the second accelerator-containing paste additionally contains from about 1 to 8% by weight of an ultraviolet absorber.

26. A chemically curable dental restorative material as defined in claim 24 wherein the second accelerator-containing paste contains about 1% by weight of a tertiary aromatic amine accelerator.

* * * * *